United States Patent [19]

White

[11] Patent Number: 4,729,761
[45] Date of Patent: Mar. 8, 1988

[54] TISSUE-IMPLANTABLE, FLUID-DISSIPATING DEVICE

[76] Inventor: Thomas C. White, 1701 S. Minnesota Ave., Sioux Falls, S. Dak. 57105-1765

[21] Appl. No.: 802,574

[22] Filed: Nov. 27, 1985

[51] Int. Cl.$^4$ .............................................. A61M 5/00
[52] U.S. Cl. ......................................... 604/8; 604/10
[58] Field of Search ................................. 604/8-10, 604/247, 294, 282

[56] References Cited

U.S. PATENT DOCUMENTS

| | | | |
|---|---|---|---|
| 2,431,587 | 11/1947 | Schnee | 604/8 |
| 3,542,026 | 11/1970 | Bledsoe | 604/247 |
| 4,240,434 | 12/1980 | Newkirk | 604/247 |
| 4,375,816 | 3/1983 | Labianca | 604/8 |
| 4,402,684 | 9/1983 | Jessup | 604/282 |
| 4,554,918 | 11/1985 | White | 604/10 |
| 4,604,087 | 8/1986 | Joseph | 604/9 |

OTHER PUBLICATIONS

Molteno, "New Implant for Drainage in Glaucoma", *Brit. J. Ophthal.*, (1969) 53, 161-168.
Molteno, "Two-Stage Insertion of Glaucoma Drainage Implants", *Trans. Ophthal. Soc. N.Z.*, vol. 31, (1979) 17-16.
Luntz, Glaucoma Surgery, Ch. 11, "Alloplastic Devices in Glaucoma Surgery: Setons", 117-123.

*Primary Examiner*—John D. Yasko
*Assistant Examiner*—Jerome R. Smith, Jr.
*Attorney, Agent, or Firm*—Gregory P. Kaihoi; Mary P. Bauman

[57] ABSTRACT

A tissue-implantable fluid-dissipating device enabling fluid from a source to be delivered to and absorbed by tissue of the eye. In one embodiment the device includes a base plate having a radius of curvature approximately equal to that of the human eye and a second plate peripherally joined to the base plate along a portion of its periphery to form an orifice, the second plate extending at least partially over but spaced from the base plate to form a cavity and having a radius of curvature less than that of the base plate. The device also includes attachment means for communicating a tube end with the cavity that is positioned to permit an attached tube to lie generally parallel to the base plate.

12 Claims, 8 Drawing Figures

TISSUE-IMPLANTABLE, FLUID-DISSIPATING DEVICE

FIELD OF THE INVENTION

The invention relates to the field of ophthalmology, and particularly to devices and methods for the relief of unusually high intraocular pressures characteristic of the disease of glaucoma.

BACKGROUND OF THE INVENTION

Glaucoma is a disease characterized by elevated intraocular pressure which, if not checked, may lead to nerve damage and visual loss. Pressures in the range of from about 15±3 mm. Hg. up to about 21 mm. Hg. may be considered to be in the normal range for human beings, whereas pressures substantially above that range are considered abnormally high. If pressures in the higher range are maintained for substantial periods of time, damage to the optic nerve of the eye may occur, leading to a narrowing of the field of vision and eventually to blindness if not appropriately treated. Although in certain cases glaucoma can be treated through the administration of certain medicines such as pilocarpine, epinephrine and timololmaleate, it is often necessary to surgically provide for the release of intraocular pressure for those patients who do not respond to drug therapy or who continue to lose vision under therapy.

Medical researchers have investigated a number of methods for the surgical release of intraocular pressure. Such surgery, in its simplest form, has involved making a small, surgical incision into the anterior chamber at or near the limbus so as to provide means for releasing an overabundance of aqueous humor from the eye into an adjacent subconjunctival space and thus to lower the intraocular pressure. In a modification of this procedure, a hair or other wicking material is reported to have been placed in the incision to provide a continuous passageway for excess fluid to be discharged from the eye. Other researchers have implanted small tubes that extend through the eye wall at the limbus or scleral-corneal junction for the purpose of providing a channel through which aqueous humor can escape. Such surgical procedures, although still used to some extent, are far from adequate. Healing of the subconjunctival drainage space frequently results in scarring, rendering the space non-absorbent of aqueous humor. When this occurs, no liquid flow through the eye wall occurs, and the intraocular pressure may hence rise to dangerous levels.

An excellent account of the history of glaucoma surgery is found in Bick, *Use of Tantalum for Ocular Drainage*, Archives of Ophthalmology 42:373-388 (1949).

In a recent embodiment, the exterior end of a tube extending through the wall of the eye is provided with a pressure relief valve in the form of small slits made through the wall of the tube at its end. Reference is made to Krupin, T., et al, *Valve Implants in Filtering Surgery*, Am. J. Ophthmol. 81:232-235, 1976. It is reported that fairly close control over the pressure needed to open the valve may be obtained. If the exterior or distal end of the tube is inserted beneath a flap of conjunctiva or the like, of course, the valved tube is subject to the same drawbacks as the other tubes described above.

Glaucoma surgeons have discovered that when surgery fails it is usually because the "bleb", the subconjunctival drainage space created by the surgeon, has become fibrosed, causing it to shrink and become non-absorbing.

One device that has been somewhat successful in maintaining the fluid absorbancy of the bleb during the healing process was described by Molteno in 1969 Molteno, "New Implant for Drainage in Glaucoma," *British Journal of Opthalmology*, Vol. 53, p. 161 (1969) described a device made from a "stellon" brand acrylic monomer. The device consisted of two parts—a flat plate fashioned to conform to the sclera and a gutter incorporated at the point where a drainage tube met the plate to assure an even spread of drainage into the bleb. In 1979, Molteno disclosed a new device that had a biconcave base plate and a long silicone tube, which served the same function as the first device. Reference is made to Chapter 11 of *Glaucoma Surgery* by Luntz, M. H., Harrison, R. and Schenker, H. I. (1984) for a description of this device.

There is a need in the medical field for a tissue-implantable device which would operate substantially on a continuous basis to permit excess aqueous humor to drain from the eye but would not be subject to the drawbacks associated with healing and scarring of tissue.

BRIEF DESCRIPTION OF THE INVENTION

The invention provides a tissue-implantable, fluid dissipating device enabling aqueous humor drained from the anterior chamber of the eye to be absorbed by tissue of the eye. The device includes a housing having walls defining an interior cavity, the housing walls having sufficient rigidity to prevent substantial collapse of the cavity when the device is implanted, orifice means communicating with the cavity to allow fluid transfer from within the cavity to surrounding fluid resorptive tissues when the device is implanted, and tube means communicating with the cavity to conduct aqueous humor to the cavity, the cavity having an inner diameter substantially greater than any inner diameter of the tube means.

The device preferably generally "floats" within the tissue pocket within which it is embedded. That is, the majority of the outer surface of the device confronts, but is not bound to, tissue which is absorptive of liquid escaping from the orifice.

When the device of the invention is surgically implanted in the eye wall, one end of the tube means communicates with the cavity, the other end communicates with the anterior chamber or with apparatus receiving aqueous humor from the anterior chamber. A fluid reservoir, for example, may collect the excess eye fluid released from the anterior chamber, and reference is made to my U.S. patent application Ser. No. 402,774 now U.S. Pat. No. 4,554,918, the teachings of which are herein incorporated by reference. In operation, fluid flows through the tube means into the interior of the cavity and thence outwardly through the orifice to be absorbed by fluid resorptive tissue facing the orifice, and desirably also tissue generally enveloping the implanted device.

The housing may be provided with a variety of configurations. In the preferred embodiment, however, the housing comprises a plate member and a hood member peripherally connected to the plate member to define a fluid-collecting, outwardly open cavity or pocket therebetween. Desirably the plate member is curved to fit the contour of the eye wall. An edge of the hood member typically extending arcuately over the plate member forms the orifice or mouth of the pocket opening. The radius of curvature of the hood member is less than the radius of curvature of the eye wall in order to form the pocket therebetween.

DETAILED DESCRIPTION

Figure 1:
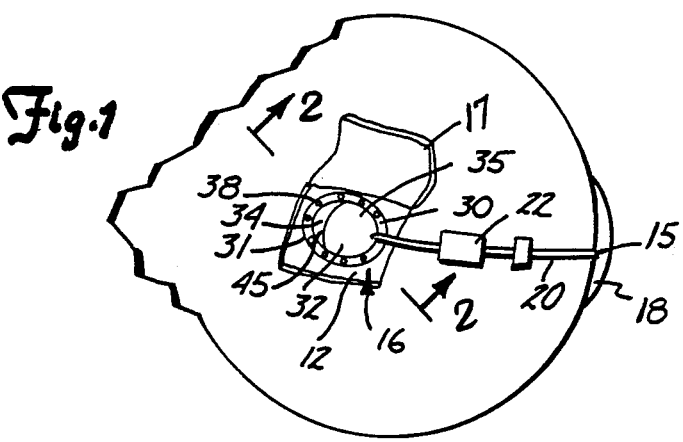
FIG. 1 is a broken-away, schematic representation of an eye showing the positioning therein of a device of the invention.

In FIG. 1, a schematic drawing of the human eye is shown generally at (10), the scleral portion being shown at (12) and the overlying conjunctiva and Tenon's Capsule together designated (17). The anterior chamber, designated (15), is filled with aqueous humor, a watery fluid. The cornea is designated (18). For clarity, other structural portions of the eye have been omitted from the drawing.

A housing (30) having walls (35) defining an interior cavity (33) is positioned against or adjacent to the outer surface of the sclera (12) beneath the conjunctiva and Tenon's Capsule (17). The housing (30) is desirably made of a pliant material such as silicone rubber, a more rigid polymeric material such as polymethyl methacrylate, an inert metal such as gold, or any other convenient and biologically acceptable material. The housing (30) is typically oval or disk-shaped with a length and width typically in the range of a centimeter or smaller. The housing walls (35) defining the interior cavity (33) have sufficient rigidity to prevent substantial collapse of the cavity when the device is implanted. Located in the housing walls (35) are orifice means (45), such as small holes with diameters of at least 0.25 mm that permit fluid transfer from within the interior cavity to fluid resorptive tissue (16) of the eye. The fluid resorptive tissues (16) of the eye include the scleral tissue (12) as well as the conjunctiva tissue (17) and other tissues of the eye.

The orifice means (45) described above include any variety of openings that may be located in the housing (30) walls (35). It may be the mouth (46) of the cavity, a hole in the housing wall, or multiple holes in the housing walls. When the device is implanted the conjunctiva and Tenon's Capsule (17) lying over the upper walls (35) of the housing do not attach to the housing (30). For this reason a space (14) exists between the tissue and the housing (30) so that fluid flowing out of the housing (30) can ideally envelope the housing (30), maximizing the surface area of resorptive tissue (16) available for contact with eye fluid. The fluid must be able to flow from the cavity to be absorbed by the tissue. The tissue of the eye will grow around the edges of the opening. If the distance between the closest inner edges of the opening measures less than 0.25 mm, the tissue growing into the opening around the edges may be able to contact other tissue and grow together, clogging the orifice means, thus effectively blocking the flow of fluid from the cavity into the surrounding tissue. In order to provide maximum drainage the orifice means must have an effective diameter of at least 0.25 mm, preferably 0.5 mm. For purposes of this application, an orifice has an effective diameter of at least 0.25 mm when an opening is defined by the orifice sized such that the opening extends at least 0.125 mm in all directions from some point within the opening. In other words if a wire circle having a diameter of 0.25 mm can be inserted through an orifice than that orifice has an effective diameter of at least 0.25 mm.

Tube means (20) communicate at one end (21) with the cavity (33) that has an inner diameter substantially greater than any inner diameter of the tube means, and a fluid reservoir at the other. The fluid reservoir may be an artificial device attached to the eye such as that shown as (22) in FIG. 1 or it may be the anterior chamber (15) of the eye itself containing aqueous humor. Excess eye fluid may flow from the anterior chamber (15) to a reservoir (22) and then into the cavity (33) of the invention through the tube means (20), or flow directly into the cavity (33) if no artificial reservoir has been attached to the eye. The orifice means includes a rim having a surface adapted to contact fluid resorptive tissue along a locus of points defining a surface representing the closest approach of fluid resorptive tissue into the cavity. The rim must be located at least approximately 0.25 mm, preferably 1.0 mm, from the housing end of the tube means.

Figure 2:
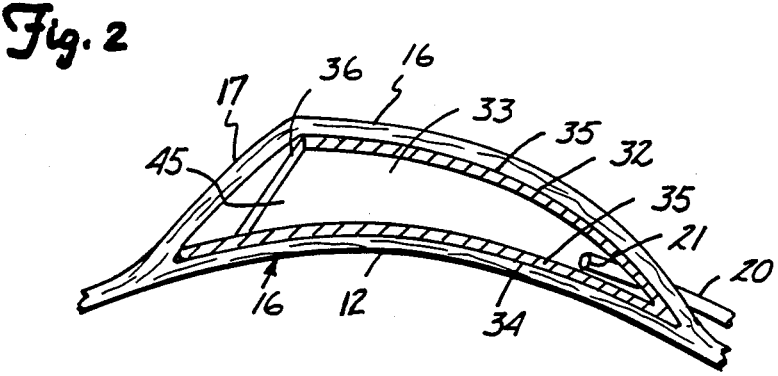
FIG. 2 is a broken-away cross-sectional view taken along line 2—2 of FIG. 1.

In the preferred embodiment shown in FIGS. 1 and 2, the housing (30) comprises a plate member (34) and a hood member (32) peripherally connected to define an interior cavity having an inner diameter substantially greater than any inner diameter of the tube means therebetween. The plate member (34) desirably is curved to fit snugly against the eye wall. The hood member (32) extends arcuately over the plate member (34) and has a radius of curvature less (about 8–10 mm) than the radius of curvature of the eye wall (about 12–15 mm) of a human eye. The arcuate edge (36) of the hood member (32) is typically rounded so that the tissue of the eye that contacts the hood member when the device is implanted in the eye will not be injured by the edge of the hood member. In this embodiment, the orifice means is the space between the plate member and the arcuate edge of the hood member and it must have an effective diameter of 0.25 mm to prevent closure by tissue. The device is implanted so that the plate member (34) contacts the sclera (12) of the eye and the exterior of the hood member (32) contacts the conjunctiva and Tenon's Capsule (17).

The plate member (34) desirably is cemented or otherwise attached to a peripheral flange (31). The flange (31) may be of silicone rubber, polymethacrylate polymer or other acceptable polymers or other convenient biologically acceptable material and may be fastened to the scleral wall by sutures or other means. The flange may have perforations (38) to receive sutures or to permit tissue ingrowth or both.

Figure 8:
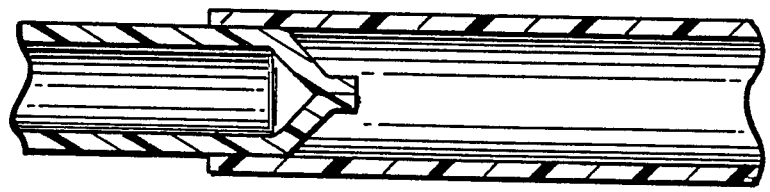
FIG. 8 shows a valve in cross-section and broken away, useful with a device of the invention.

The tube means (20) preferably includes a unidirectional check valve shown in FIG. 8 to permit fluid to flow into the interior cavity (33) of the housing (30) only. In the device shown in FIGS. 1 and 2, the tube means (20) can establish communication with the interior cavity (33) from any position as long as the end (21) (the last portion of the tube means that has an inner cross-sectional area that is substantially equal to the inner cross-sectional area of the rest of the tube means) remains at least 0.25 mm away from the orifice rim.

Figure 3:
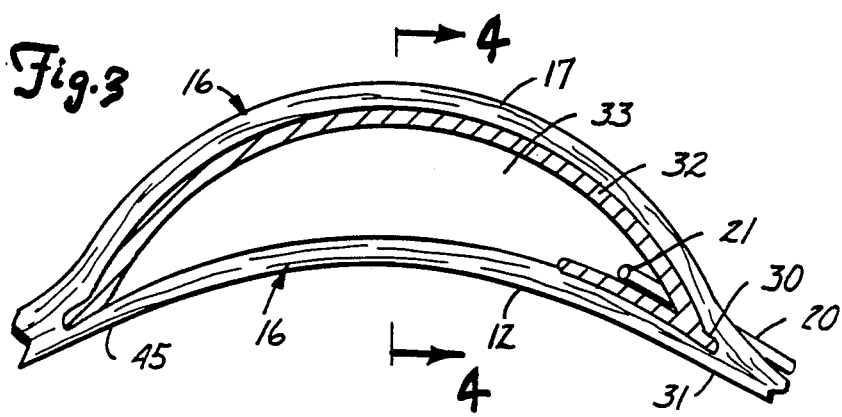
FIG. 3 is a broken-away cross-sectional view of another embodiment of the invention.
Figure 4:
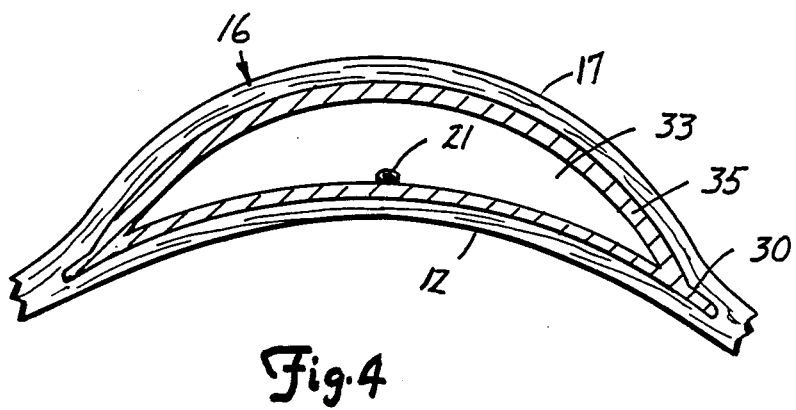
FIG. 4 is a broken-away cross-sectional view taken along line 4—4 of FIG. 3.

In another embodiment of the device shown at FIGS. 3 and 4, the housing (30) comprises a hood member (32) having a maximum radius of curvature less than the radius of curvature of the eye wall of the human eye. The hood member (32) will thus be concave and will define an interior cavity (33) having an inner diameter substantially greater than any inner diameter of the tube means between the scleral wall (12) and the interior walls of the hood member. The peripheral edge of the hood member (32) will be attached to the scleral wall. The orifice means (45) in this embodiment is defined by the inner peripheral edge (47) of the walls of the hood member, the sclera (12) of the eye providing the resorptive tissue interface to allow fluid absorption. A peripheral flange (21) may be peripherally cemented or otherwise attached to the edge of the hood member (32) or the hood member (32) may itself have a flat surface around its peripheral edge so that the hood member may be attached to the scleral wall (12) of the eye forming an interior cavity (33) within the walls (35) of the hood. Attached to an inner wall of the hood member (32) may be a plate member (34) that would permit the housing end of the tube means (20) to communicate with the cavity (33) and yet be spaced at least 0.25 mm from the sclera (12) or any other resorptive tissue in any direction. Although a plate member is shown, it would not be necessary if the tube means end communicates with the housing from the top or sides as long as the end of the tube means is kept at least 0.25 mm from the sclera.

Figure 5:
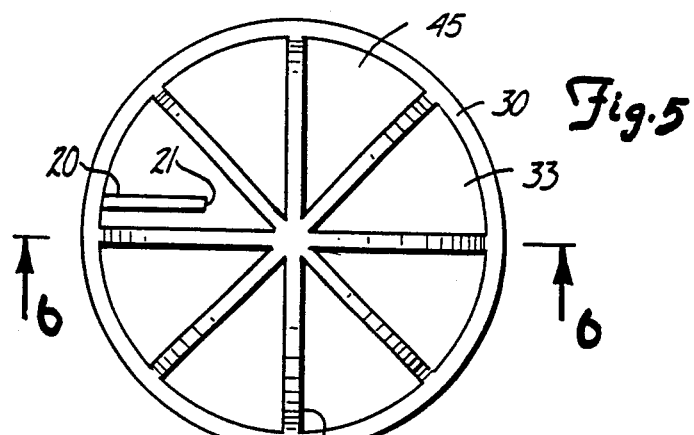
FIG. 5 is a plan view of another device of the invention.
Figure 6:
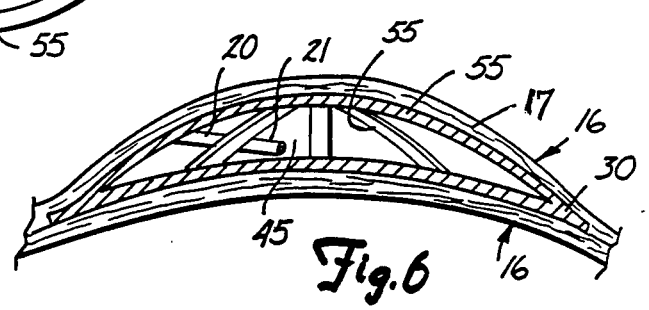
FIG. 6 is a broken-away cross-sectional view taken along line 6—6 of FIG. 5.

In another embodiment of the invention shown in FIGS. 5 and 6, the housing (30) comprises a plate member (34), preferably oval or disk-shaped, to which a plurality of support structures (55) are attached at its peripheral edge that extend arcuately over the plate member to define an interior cavity (33) and meeting in a common point. This device resembles a cage. The support structures (55) are of sufficient rigidity to prevent substantial collapse of the cavity when the device is implanted. In the context of this application, preventing substantial collapse means that although the housing may undergo some deformation, the cavity and orifice means remain open and the 0.25 mm limitation with respect to the orifice means are continuously met. The open space between support structures (55) must have an effective diameter of at least about 0.25 mm so that tissue overlying the support structures (55) will not form a bridge between the support structures (55) and the drainage area will remain open. The tube means (20) should communicate with the housing in such a way that the support structures (55) will protect the tube means (20) from contacting resorptive tissue of the eye and thus prevent tissue from growing over the tube end and preventing fluid flow. In other words the rim of the orifice means (the space between support structures) must be at least about 0.25 mm away from the housing end of the tube means.

Figure 7:
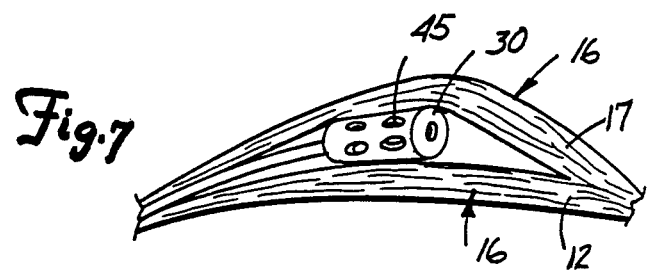
FIG. 7 shows another embodiment of the invention.

In another embodiment of the invention shown in FIG. 7, the housing may be an extension of the tube means. In this device the housing has walls that define a cavity having an inner diameter substantially greater than any inner diameter of the tube means and orifice means, the cavity and the orifice having a cross-sectional area available for fluid flow substantially greater than that of the interior of the tube means. The housing walls extending from the walls of the tube means must have sufficient rigidity to prevent substantial collapse of the cavity when the device is implanted. Orifice means located in the housing walls must have an effective diameter of at least 0.25 mm and the rim must be at least about 0.25 mm away from the end of the tube means.

This invention may be used with artificial pressurized reservoirs used by glaucoma surgeons to relieve ocular pressure such as that shown in my U.S. patent application Ser. No. 402,774. The reservoir includes a check valve on both its posterior and anterior ends which permits fluid to flow only in one direction away from the anterior chamber of the eye. The reservoir will accumulate fluid. When the reservoir is pressurized by digital manipulation, such manipulation causes the pressure in the reservoir to substantially rise and to force fluid from the reservoir through the tube means into the housing cavity and into the resorptive tissue of the eye through the orifice means located in the housing.

Many other types of housings may be used so that the device serves the same purpose of protecting the end of the tube means from being clogged through contact with tissue of the eye. Briefly, some other varieties may include a device in which the tube means separates into two separate portions at the housing end so that there are two or more ends located within the housing. Typically the two ends will form a "T" within the housing of the device.

While a preferred embodiment of the present invention has been described, it should be understood that various changes, adaptations, and modifications may be made therein without departing from the spirit of the invention and the scope of the appended claims.

What is claimed is:
1. An ocular tissue-implantable, fluid-dissipating device comprising:
a base plate having a radius of curvature approximately equal to that of the human eye; a second plate peripherally joined to the base plate along a portion of the periphery of the base plate to form an outwardly open orifice, the second plate extending at least partially over but spaced from the base plate to form a cavity, said second plate having a radius of curvature less than that of the base plate; and tube attachment means for communicating the end of a tube with the cavity to allow fluid flow therebetween, the tube attachment means being positioned to permit an attached tube to lie generally parallel to the base plate.

2. The device of claim 1 wherein the orifice has an effective diameter of at least about 0.25 mm.

3. The device of claim 1 wherein the orifice includes a rim adapted to contact fluid resorptive tissue, said rim defining a surface representing the closest approach of fluid resorptive tissue into the cavity.

4. The device of claim 1 wherein the second plate extends arcuately over the base plate.

5. The device of claim 4 wherein the arcuate edge of the second plate is rounded to reduce trauma to contiguous eye tissue.

6. The device of claim 1 including attachment means for attaching the device to the wall of an eye.

7. The device of claim 1 including tube means communicating with a cavity for conducting fluid into the cavity, said tube means having a one-way valve for enabling fluid flow only into the cavity.

8. A tissue-implantable, fluid-dissipating device comprising:
a curved housing having a peripheral portion and a central portion having a radius of curvature which is substantially less than the radius of the curvature of a human eye, resulting in the formation of a concave cavity between the eye wall and housing when the housing peripheral portion is in contact with the eye wall; attachment means carried by the housing for attaching the housing to the eye wall and tube means communicating with the housing so that fluid may flow into the housing from another part of the eye.

9. The device of claim 8 wherein the surface area of the eye wall comprising fluid resorptive tissue within the housing has an effective diameter of at least about 0.25 mm.

10. An ocular tissue-implantable fluid-dissipating device comprising:
a base plate having a radius of curvature approximately equal to that of the human eye; a second plate peripherally joined to the base plate along a portion of the periphery of the base plate to form an outwardly open orifice; the second plate extending at least partially over but spaced from the base plate to form an interior cavity, said second plate having a radius of curvature less than that of the base plate; a limp, expandable, compressible reservoir, and tube means communicating the reservoir with the cavity to allow fluid to flow from the reservoir into the cavity, said tube means being positioned generally parallel to the base plate.

11. The device of claim 10 including a one-way valve carried by the tube means for enabling fluid flow only into the cavity.

12. A tissue-implantable, fluid-dissipating device comprising:
a housing having a peripheral portion and a central portion and shaped to be placed on an eye wall so that a cavity is defined between the eye wall and the housing when the housing peripheral portion is in contact with at least a portion of the eye wall; attachment means carried by the housing for attaching the housing to the eye wall and tube means communicating with the housing for conducting fluid into the cavity.

* * * * *